United States Patent
Schaefferkoetter

(10) Patent No.: US 11,854,126 B2
(45) Date of Patent: Dec. 26, 2023

(54) METHODS AND APPARATUS FOR DEEP LEARNING BASED IMAGE ATTENUATION CORRECTION

(71) Applicant: Siemens Medical Solutions USA, Inc., Malvern, PA (US)

(72) Inventor: Joshua Schaefferkoetter, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 341 days.

(21) Appl. No.: 17/305,395

(22) Filed: Jul. 7, 2021

(65) Prior Publication Data
US 2023/0009528 A1 Jan. 12, 2023

(51) Int. Cl.
*G06T 11/00* (2006.01)
*G06T 7/00* (2017.01)
(Continued)

(52) U.S. Cl.
CPC .............. *G06T 11/008* (2013.01); *G06N 3/08* (2013.01); *G06T 3/0068* (2013.01); *G06T 7/0012* (2013.01); *G06T 2207/10104* (2013.01); *G06T 2207/20081* (2013.01); *G06T 2207/20084* (2013.01)

(58) Field of Classification Search
CPC ... G06T 11/008; G06T 3/0068; G06T 7/0012; G06T 2207/10104; G06T 2207/20081; G06T 2207/20084; G06T 11/005; G06N 3/08; A61B 6/5229; A61B 6/032; A61B 6/466; A61B 6/037; G01R 33/481
See application file for complete search history.

(56) References Cited

U.S. PATENT DOCUMENTS

| 8,620,053 B2 | 12/2013 | Michel et al. |
| 9,872,664 B1 * | 1/2018 | Jin .................... A61B 6/5282 |

(Continued)

OTHER PUBLICATIONS

Leynes, A.P., et al., Zero-echo-time and Dixon deep pseudo-CT (ZeDD CT): direct generation of pseudo-CT images for pelvic PET/MRI attenuation correction using deep convolutional neural networks with multiparametric MRI. Journal of Nuclear Medicine, 2018. 59(5): p. 852-858.

(Continued)

*Primary Examiner* — Van D Huynh

(57) ABSTRACT

Systems and methods for reconstructing medical images are disclosed. Measurement data from positron emission tomography (PET) data, and measurement data from an anatomy modality, such as magnetic resonance (MR) data or computed tomography (CT) data, is received from an image scanning system. A PET image is generated based on the PET measurement data, and an anatomy image is generated based on the anatomy measurement data. A trained neural network is applied to the PET image and the anatomy image to generate an attenuation map. The neural network may be trained based on anatomy and PET images. In some examples, the trained neural network generates an initial attenuation map based on the anatomy image, registers the initial attenuation map to the PET image, and generates an enhanced attenuation map based on the registration. Further, a corrected image is reconstructed based on the generated attenuation map and the PET image.

20 Claims, 9 Drawing Sheets

(51) Int. Cl.
*G06T 3/00* (2006.01)
*G06N 3/08* (2023.01)

(56) References Cited

U.S. PATENT DOCUMENTS

| | | | | |
|---|---|---|---|---|
| 2003/0004405 | A1* | 1/2003 | Townsend | A61B 6/463 600/407 |
| 2008/0107229 | A1* | 5/2008 | Thomas | A61B 6/037 378/207 |
| 2011/0103669 | A1* | 5/2011 | Michel | G06T 11/005 382/131 |
| 2011/0158497 | A1* | 6/2011 | Schweizer | G01T 1/1603 382/131 |
| 2011/0288407 | A1* | 11/2011 | Brinks | G01T 1/1611 378/4 |
| 2018/0025512 | A1* | 1/2018 | Zhu | G06T 7/11 382/131 |
| 2018/0374205 | A1* | 12/2018 | Zhu | G06T 5/007 |
| 2019/0012811 | A1* | 1/2019 | Wang | G06T 11/003 |
| 2019/0304144 | A1* | 10/2019 | Feng | G06T 7/174 |
| 2020/0126231 | A1* | 4/2020 | Hu | G06T 5/50 |
| 2022/0207791 | A1* | 6/2022 | Shi | A61B 6/037 |

OTHER PUBLICATIONS

Armanious, K., et al., Independent attenuation correction of whole body [18 F] FDG-PET using a deep learning approach with Generative Adversarial Networks. EJNMMI research, 2020. 10: p. 1-9.

Hwang, D., et al., Generation of PET attenuation map for whole-body time-of-flight 18F-FDG PET/MRI using a deep neural network trained with simultaneously reconstructed activity and attenuation maps. Journal of Nuclear Medicine, 2019. 60(8): p. 1183-1189.

Zhu, J.-Y., et al. Unpaired image-to-image translation using cycle-consistent adversarial networks. in Proceedings of the IEEE international conference on computer vision. 2017.

Armanious, K., et al. Unsupervised medical image translation using Cycle-MedGAN. in 2019 27th European Signal Processing Conference (EUSIPCO). 2019. IEEE.

Wolterink, J.M., et al. Deep MR to CT synthesis using unpaired data. in International workshop on simulation and synthesis in medical imaging. 2017. Springer.

Ge, Y., et al. Unpaired whole-body MR to CT synthesis with correlation coefficient constrained adversarial learning. in Medical Imaging 2019: Image Processing. 2019. International Society for Optics and Photonics.

Dong, X., et al., Deep learning-based attenuation correction in the absence of structural information for whole-body positron emission tomography imaging. Physics in Medicine & Biology, 2020. 65(5): p. 055011.

* cited by examiner

METHODS AND APPARATUS FOR DEEP LEARNING BASED IMAGE ATTENUATION CORRECTION

FIELD

Aspects of the present disclosure relate in general to medical diagnostic systems and, more particularly, to reconstructing images from nuclear imaging systems for diagnostic and reporting purposes.

BACKGROUND

Nuclear imaging systems can employ various technologies to capture images. For example, some nuclear imaging systems employ positron emission tomography (PET) to capture images. PET is a nuclear medicine imaging technique that produces tomographic images representing the distribution of positron emitting isotopes within a body. Some nuclear imaging systems employ computed tomography (CT), for example, as a co-modality. CT is an imaging technique that uses x-rays to produce anatomical images. Magnetic Resonance Imaging (MRI) is an imaging technique that uses magnetic fields and radio waves to generate anatomical and functional images. Some nuclear imaging systems combine images from PET and CT scanners during an image fusion process to produce images that show information from both a PET scan and a CT scan (e.g., PET/CT systems). Similarly, some nuclear imaging systems combine images from PET and MRI scanners to produce images that show information from both a PET scan and an MRI scan.

Typically, these nuclear imaging systems capture measurement data, and process the captured measurement data using mathematical algorithms to reconstruct medical images. For example, reconstruction can be based on the models that can include analytic or iterative algorithms or, more recently, deep learning algorithms. These conventional models, however, can have several drawbacks. Many of these nuclear imaging systems, for example, have high memory and computational requirements to reconstruct a medical image. Moreover, many image formation processes employed by at least some of these systems rely on approximations to compensate for detection loss. The approximations, however, can cause inaccurate and lower quality medical images. As such, there are opportunities to address deficiencies in nuclear imaging systems.

SUMMARY

Systems and methods for generating attenuation maps based on deep learning processes to reconstruct medical images are disclosed.

In some embodiments, a computer-implemented method includes receiving positron emission tomography (PET) measurement data from an image scanning system. The method also includes receiving modality measurement data from the image scanning system. The method also includes training a neural network based on the modality measurement data and the PET measurement data. The method further includes storing the trained neural network in a data repository.

In some embodiments, a computer-implemented method includes receiving positron emission tomography (PET) measurement data and anatomy measurement data from an image scanning system. The method further includes generating PET images based on the PET measurement data and anatomy images based on the anatomy measurement data. The method also includes training a neural network with the PET images and the anatomy images. Further, the method includes storing the trained neural network in a data.

In some embodiments, a non-transitory computer readable medium stores instructions that, when executed by at least one processor, cause the at least one processor to perform operations including receiving positron emission tomography (PET) measurement data and anatomy measurement data from an image scanning system. The operations further include generating PET images based on the PET measurement data and anatomy images based on the anatomy measurement data. The operations also include training a neural network with the PET images and the anatomy images. Further, the operations include storing the trained neural network in a data repository.

In some embodiments, a non-transitory computer readable medium stores instructions that, when executed by at least one processor, cause the at least one processor to perform operations including receiving modality measurement data and positron emission tomography (PET) measurement data from an image scanning system. Further, the operations include applying a trained neural network to the modality measurement data and the PET measurement data to generate an enhanced attenuation map. The operations also include generating image volume data based on the enhanced attenuation map and the PET measurement data. The operations further include storing the image volume data in a data repository.

In some embodiments, a system includes a data repository and at least one processor communicatively coupled the data repository. The at least one processor is configured to receive positron emission tomography (PET) measurement data from an image scanning system. The at least one processor is also configured to receive modality measurement data from the image scanning system. The at least one processor is further configured to train a neural network based on the modality measurement data and the PET measurement data. Further, the at least one processor is configured to store the trained neural network in the data repository.

In some embodiments, a system comprises a database and at least one processor communicatively coupled to the database. The at least one processor is configured to receive positron emission tomography (PET) measurement data and anatomy measurement data from an image scanning system. The at least one processor is further configured to generate PET images based on the PET measurement data and anatomy images based on the anatomy measurement data. The at least one processor is also configured to train a neural network with the PET images and the anatomy images. Further, the at least one processor is configured to store the trained neural network in a data repository.

BRIEF DESCRIPTION OF THE DRAWINGS

The following will be apparent from elements of the figures, which are provided for illustrative purposes and are not necessarily drawn to scale.

DETAILED DESCRIPTION

Figure 1A:
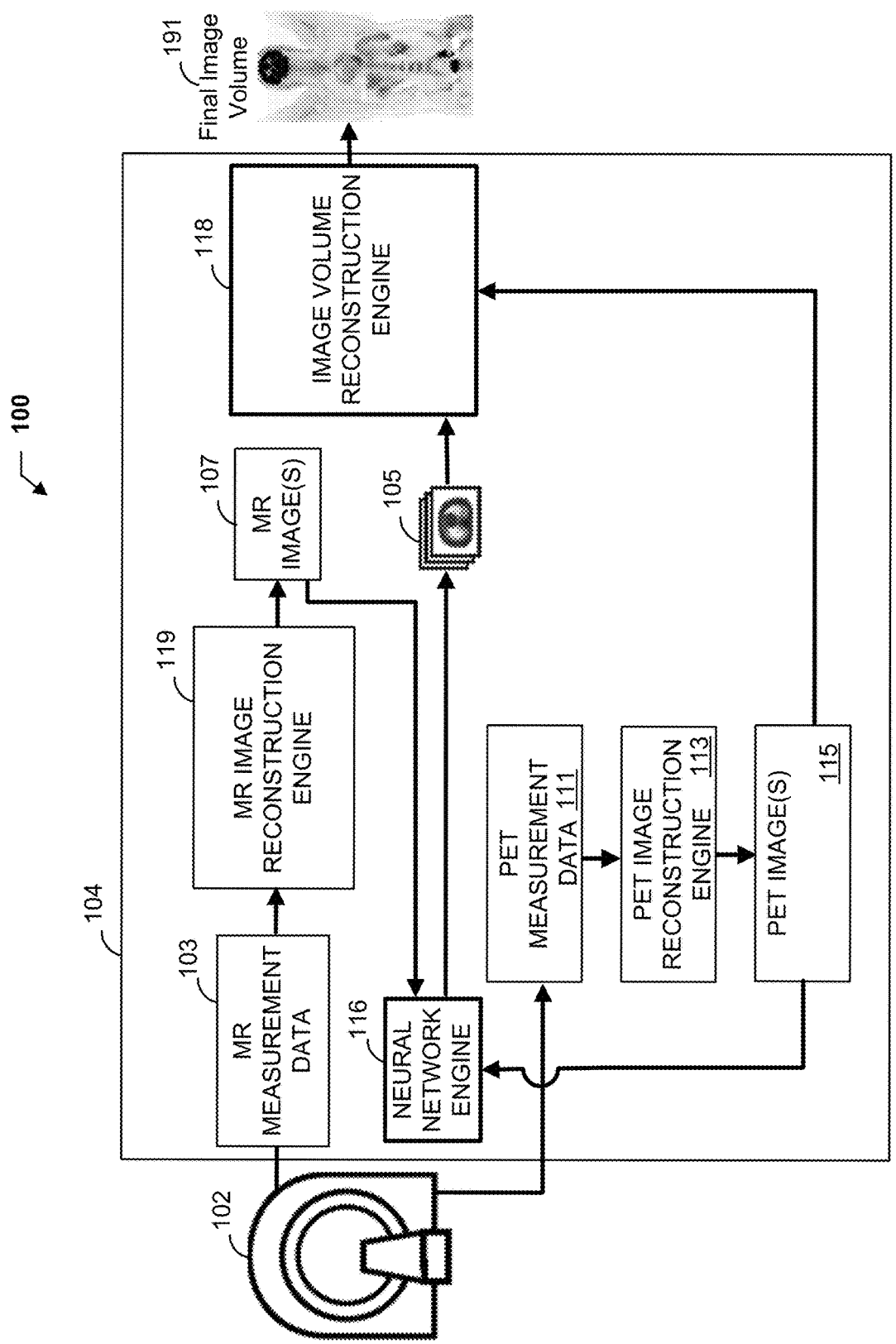
FIGS. 1A and 1B illustrate a nuclear image reconstruction system, in accordance with some embodiments.

This description of the exemplary embodiments is intended to be read in connection with the accompanying drawings, which are to be considered part of the entire written description.

The exemplary embodiments are described with respect to the claimed systems as well as with respect to the claimed methods. Furthermore, the exemplary embodiments are described with respect to methods and systems for image reconstruction, as well as with respect to methods and systems for training functions used for image reconstruction. Features, advantages, or alternative embodiments herein can be assigned to the other claimed objects and vice versa. For example, claims for the providing systems can be improved with features described or claimed in the context of the methods, and vice versa. In addition, the functional features of described or claimed methods are embodied by objective units of a providing system. Similarly, claims for methods and systems for training image reconstruction functions can be improved with features described or claimed in context of the methods and systems for image reconstruction, and vice versa.

Various embodiments of the present disclosure can employ machine learning methods or processes to provide clinical information from nuclear imaging systems. For example, the embodiments can employ machine learning methods or processes to reconstruct images based on captured measurement data, and provide the reconstructed images for clinical diagnosis. In some embodiments, machine learning methods or processes are trained, to improve the reconstruction of images.

Quantitative Positron Emission Tomography (PET) generally requires an attenuation map to correct for a number of photons that have either been lost for a sinogram bin (i.e., attenuation correction) or wrongly assigned to another sinogram bin (i.e., scatter correction). The corrections generally depend on an accurate knowledge of photon values within a subject. The attenuation map characterizing the corrections (e.g., mu map) is calculated or estimated using an accompanying anatomical modality, such as computed tomography (CT) or magnetic resonance (MR). Current methods for MR-based attenuation correction are subject to many well-known issues, including inaccurate attenuation values, tissue misclassification, and incomplete or misregistered bone atlases. Moreover, current methods may be prone to additional errors associated with spatial inconsistencies between anatomy and PET images due to different scanning time points.

In some embodiments, a machine learning model, such as a neural network, can be trained to generate attenuation maps based on modality measurement data (e.g., CT measurement or MR measurement data) and PET measurement data. For example, the machine learning model may be trained based on PET measurement data and corresponding MR measurement data captured from a PET/MR system (e.g., using volunteer subjects or using previously stored imaging data). In some examples, the machine learning model is trained based on PET measurement data and corresponding CT measurement data (e.g., for a PET/CT imaging system). Once the machine learning model is trained, the system (e.g., the PET/MR or PET/CT system) can be employed for clinical imaging.

In some examples, deep learning processes are employed for generating PET attenuation correction data, transforming both functional and morphological information simultaneously into maps of attenuation values (e.g., mu maps with 511 keV attenuation values). Among other advantages, the combination of modalities (e.g., PET and MR or PET and CT) provides additional information for estimating the attenuation correction data, as the generated maps are informed by the anatomical structure and are optimized to match the (uncorrected) PET distribution. Moreover, the embodiments may substantially improve misregistration errors (e.g., mismatches in location or size of organs, banana artefact at liver dome) over current methods for static imaging, and may also allow for time-frame-adaptive attenuation correction for dynamic, motion-corrected, and gated PET studies. Furthermore, the machine learning model may be trained to generate attenuation correction maps for any imaging domain, yielding, for example, a single attenuation correction approach for both PET/CT and PET/MR systems.

In addition, the embodiments may provide higher quality attenuation and scatter corrections leading to more reliable PET quantification, inherent elastic registration for optimizing the quantitative mu maps to a PET's frame of reference, and the applicability of the processes described herein to both PET/CT and PET/MR systems.

In some embodiments, a scanning device, such as a PET/MR scanner, provides PET measurement data, such as three-dimensional (3D) time-of-flight sinograms (e.g., measurement data), to a computing device. The PET/MR scanner can also capture MR images, and provide corresponding MR measurement data to the computing device. The computing device can apply a trained neural network, such as a trained deep learning neural network, to the PET measurement data and the MR measurement data to generate an attenuation correction map (e.g., mu map). Further, the computing device can generate an image volume (e.g., a 3 dimensional image) based on the generated attenuation map and the PET measurement data.

In some embodiments, a PET/CT scanner provides PET measurement data and CT measurement data to a computing device. The computing device can apply a trained neural network, such as a trained deep learning neural network, to the PET measurement data and the CT measurement data to generate an attenuation correction map. Further, the computing device can generate an image volume based on the generated attenuation map and the PET measurement data.

As described herein, the trained neural network may include a transformation stage and a registration stage. The transformation stage may generate an initial attenuation correction map based on modality correction data (e.g., MR measurement data or CT measurement data). At the registration state, a final (e.g., enhanced) attenuation map is generated based on the initial attenuation map and the PET measurement data.

In some examples, multiple neural networks are trained based on one or more attributes of patients. For example, a neural network may be trained based on MR measurement data and PET measurement data corresponding to one or more of person's within a particular age range, weight range, height range, body part (e.g., chest, head, arm, leg, etc.), and medical condition. As an example, a first neural network can be trained based on MR measurement data and PET measurement data for persons under the age of 16, and a second neural network can be trained based on MR measurement data and PET measurement data for persons between the ages of 16 and 21, and a third neural network can be trained based on MR measurement data and PET measurement data for persons above the age of 21. During diagnosis of a patient, the appropriate neural network may be employed by the computing device to generate image volumes, as described herein. In some examples, parameters, such as a parameter identifying a patient's age, weight, height, medical condition, or body part, may be provided as an input to a trained neural network that is correspondingly trained to generate attenuation maps based on the provided input (e.g., the computing device may generate a feature based on the patient's age, and provide the generated feature to the trained neural network).

In some examples, the computing device validates the trained neural network during a validation period. For example, the computing device can apply the neural network to MR measurement data and PET measurement data obtained from a validation test data set to generate a predicted attenuation correction map. The computing device can further determine a loss (e.g., by applying a loss function) between the predicted attenuation map and an expected attenuation map (e.g., the expected attenuation map could have been generated based on prior art processes). Training of the neural network can be complete when the loss (e.g., as indicated by the output of a loss function) has been minimized to at least a threshold (e.g., to below a predetermined threshold). Once trained, the computing device can apply the trained neural network to modality measurement data and PET measurement data to generate attenuation maps.

In some examples, the PET measurement data is acquired using the PET modality of a combined PET/MR system that allows acquisition of PET and MR measurement data. In some examples, the PET data is acquired using the PET modality of a combined PET/CT system that allows acquisition of PET and CT measurement data.

For example, the PET/MR scanner can capture MR scans and PET scans (e.g., synthetic 511 keV transmission images) of a patient (e.g., a patient injected with radioactive material), and can transmit corresponding MR measurement data and PET measurement data to the computing device. The computing device reconstructs an MR image based on the MR measurement data, and further applies the trained neural network to the MR measurement data and the PET measurement data to generate an attenuation map. The computing device then reconstructs an image volume based on the attenuation map and the reconstructed MR image. The computing device can store the image volume in a data repository. The computing device can also display the image volume to a physician for evaluation and diagnosis, for example.

In some examples, a PET/CT scanner can capture CT scans and PET scans of a patient, and can transmit corresponding CT measurement data and PET measurement data to the computing device. The computing device reconstructs an CT image based on the CT measurement data, and further applies the trained neural network to the CT measurement data and the PET measurement data to generate an attenuation map. The computing device then reconstructs an image volume based on the attenuation map and the reconstructed CT image. The computing device can store the image volume in a data repository. The computing device can also display the image volume to a physician for evaluation and diagnosis, for example.

Figure 1B:
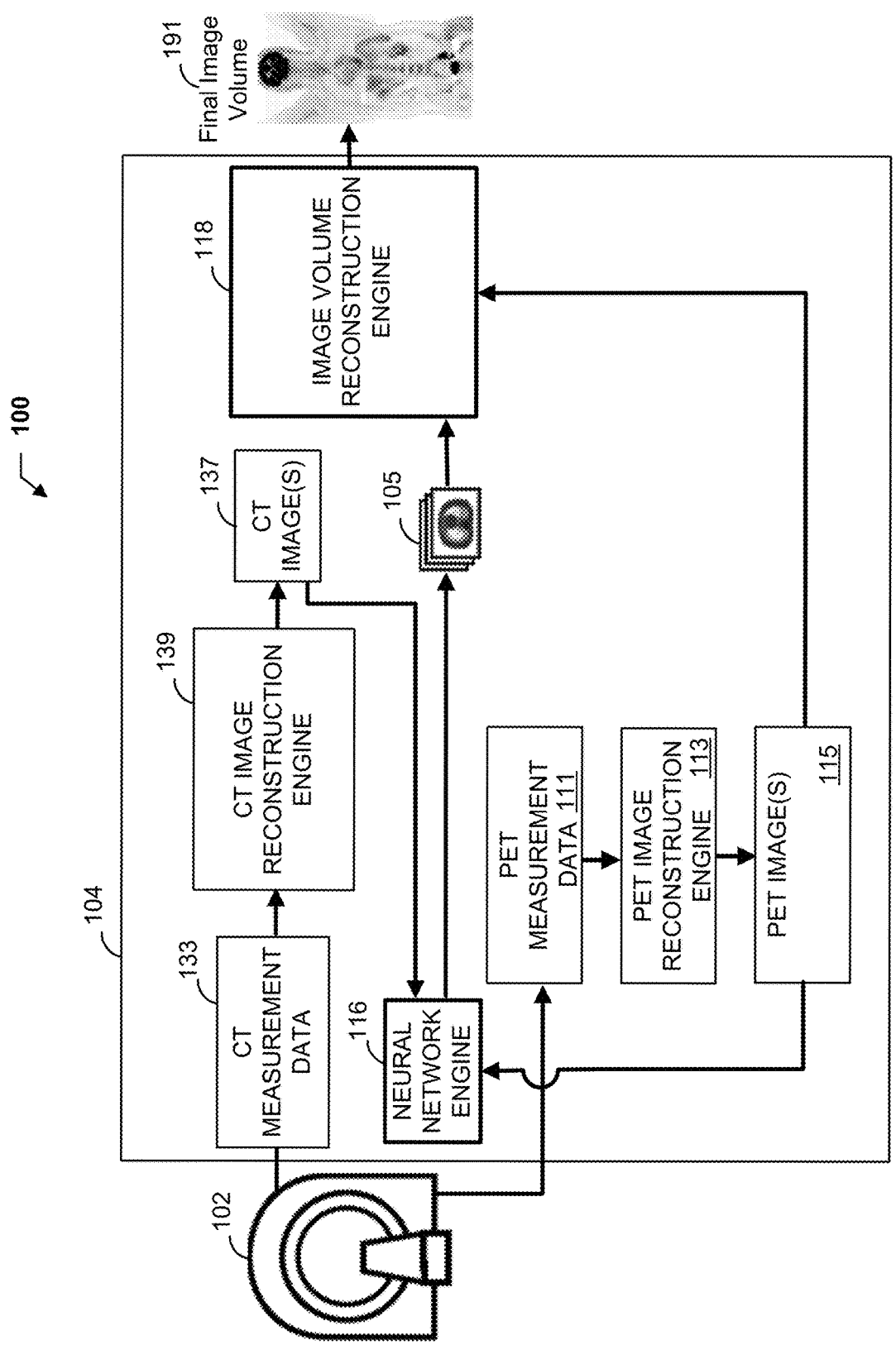

FIG. 1A illustrates one embodiment of a nuclear imaging system 100. As illustrated, nuclear imaging system 100 includes image scanning system 102 and image reconstruction system 104. Image scanning system 102, in this example, can be a PET/MR scanner that can capture PET and MR images. In FIG. 1B, image scanning system 102 is a PET/CT scanner that can capture PET and CT images.

Referring to FIG. 1A, image scanning system 102 can capture the MR images (e.g., of a person), and generate MR measurement data 103 based on the MR scans. Image scanning system 102 can also capture PET images (e.g., of the person), and generate PET measurement data 111 (e.g., PET raw data, such as sinogram data) based on the captured PET images. The PET measurement data 111 can represent anything imaged in the scanner's field-of-view (FOV) containing positron emitting isotopes. For example, the PET measurement data 111 can represent whole-body image scans, such as image scans from a patient's head to thigh. Image scanning system 102 can transmit the MR measurement data 103 and the PET measurement data 111 to image reconstruction system 104.

In some examples, all or parts of image reconstruction system 104 are implemented in hardware, such as in one or more field-programmable gate arrays (FPGAs), one or more application-specific integrated circuits (ASICs), one or more state machines, one or more computing devices, digital circuitry, or any other suitable circuitry. In some examples, parts or all of image reconstruction system 104 can be implemented in software as executable instructions such that, when executed by one or more processors, cause the one or more processors to perform respective functions as described herein. The instructions can be stored in a non-transitory, computer-readable storage medium, for example.

Figure 2:
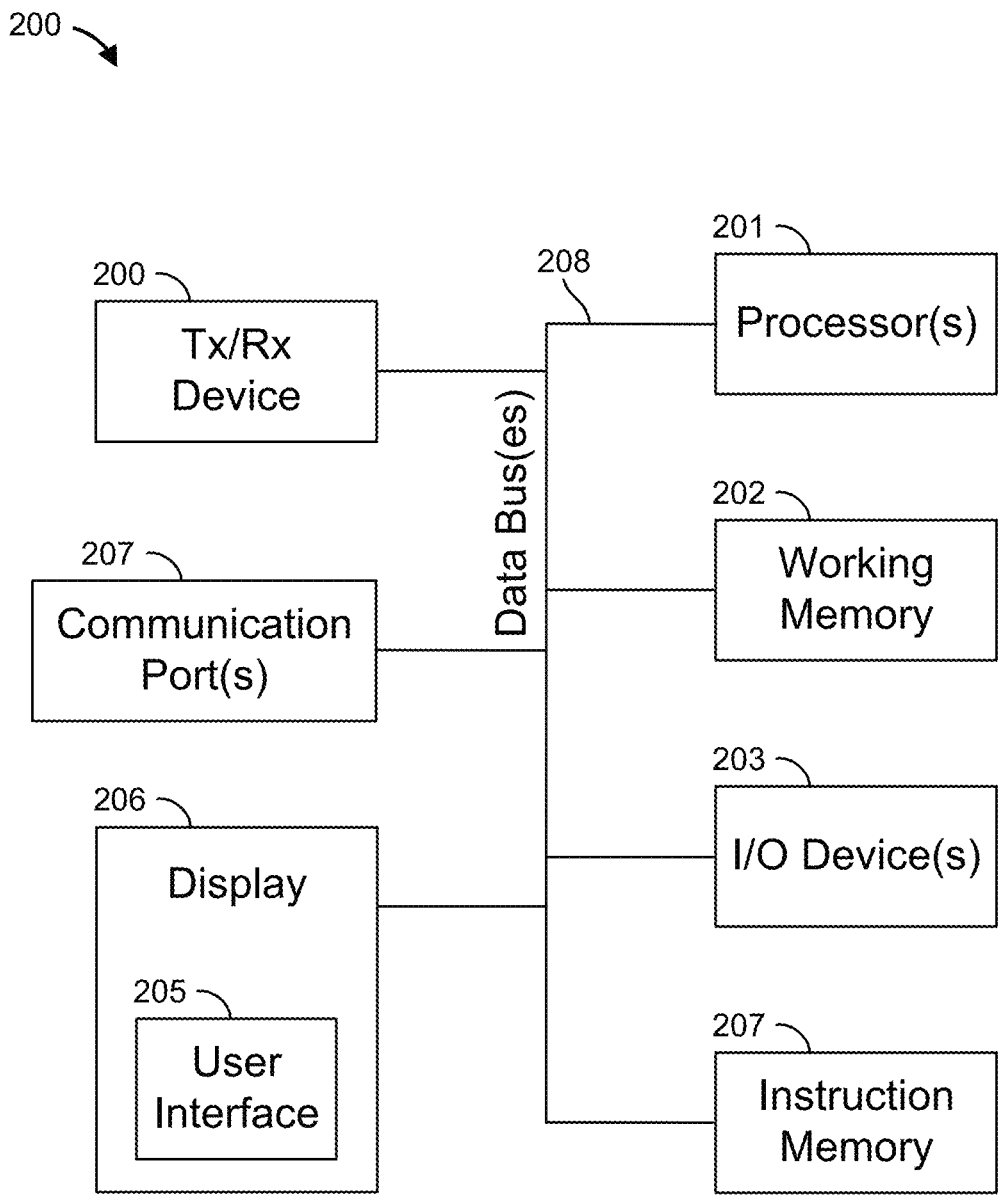
FIG. 2 illustrates a block diagram of an example computing device that can perform one or more of the functions described herein, in accordance with some embodiments.

For example, FIG. 2 illustrates a computing device 200 that can be employed by the image reconstruction system 104. Computing device 200 can implement, for example, one or more of the functions of image reconstruction system 104 described herein.

Computing device 200 can include one or more processors 201, working memory 202, one or more input/output devices 203, instruction memory 207, a transceiver 204, one or more communication ports 207, and a display 206, all operatively coupled to one or more data buses 208. Data buses 208 allow for communication among the various devices. Data buses 208 can include wired, or wireless, communication channels.

Processors 201 can include one or more distinct processors, each having one or more cores. Each of the distinct processors can have the same or different structure. Processors 201 can include one or more central processing units (CPUs), one or more graphics processing units (GPUs), application specific integrated circuits (ASICs), digital signal processors (DSPs), and the like.

Processors 201 can be configured to perform a certain function or operation by executing code, stored on instruction memory 207, embodying the function or operation. For example, processors 201 can be configured to perform one or more of any function, method, or operation disclosed herein.

Instruction memory 207 can store instructions that can be accessed (e.g., read) and executed by processors 201. For example, instruction memory 207 can be a non-transitory, computer-readable storage medium such as a read-only memory (ROM), an electrically erasable programmable read-only memory (EEPROM), flash memory, a removable disk, CD-ROM, any non-volatile memory, or any other suitable memory. For example, instruction memory 207 can store instructions that, when executed by one or more processors 201, cause one or more processors 201 to perform one or more of the functions of image reconstruction system 104, such as one or more of the encoding segment 120 functions, one or more of the Radon inversion layer 140 functions, or one or more of the refinement and scaling segment 160 functions.

Processors 201 can store data to, and read data from, working memory 202. For example, processors 201 can store a working set of instructions to working memory 202, such as instructions loaded from instruction memory 207. Processors 201 can also use working memory 202 to store dynamic data created during the operation of computing device 200. Working memory 202 can be a random access memory (RAM) such as a static random access memory (SRAM) or dynamic random access memory (DRAM), or any other suitable memory.

Input-output devices 203 can include any suitable device that allows for data input or output. For example, input-output devices 203 can include one or more of a keyboard, a touchpad, a mouse, a stylus, a touchscreen, a physical button, a speaker, a microphone, or any other suitable input or output device.

Communication port(s) 207 can include, for example, a serial port such as a universal asynchronous receiver/transmitter (UART) connection, a Universal Serial Bus (USB) connection, or any other suitable communication port or connection. In some examples, communication port(s) 207 allows for the programming of executable instructions in instruction memory 207. In some examples, communication port(s) 207 allow for the transfer (e.g., uploading or downloading) of data, such as Mill measurement data 103 and attenuation maps 105.

Display 206 can display user interface 205. User interfaces 205 can enable user interaction with computing device 200. For example, user interface 205 can be a user interface for an application that allows for the viewing of final image volumes 191. In some examples, a user can interact with user interface 205 by engaging input-output devices 203. In some examples, display 206 can be a touchscreen, where user interface 205 is displayed on the touchscreen.

Transceiver 204 allows for communication with a network, such as a Wi-Fi network, an Ethernet network, a cellular network, or any other suitable communication network. For example, if operating in a cellular network, transceiver 404 is configured to allow communications with the cellular network. Processor(s) 401 is operable to receive data from, or send data to, a network via transceiver 204.

Referring back to FIG. 1A, image reconstruction system 104 includes neural network engine 116, MR image reconstruction engine 119, PET image reconstruction engine 113, and image volume reconstruction engine 118. MR image reconstruction engine 119 operates on MR measurement data 103 (e.g., MR raw data) to generate reconstructed MR image 107. MR image reconstruction engine 119 can generate reconstructed MR images 107 based on corresponding MR measurement data 103 using any suitable method (e.g., algorithm) known in the art. Similarly, PET image reconstruction engine 113 operates on PET measurement data 111 to generate reconstructed PET image 115. PET image reconstruction engine 113 can generate reconstructed PET images 115 based on corresponding PET measurement data 111 using any suitable method known in the art.

Further, neural network engine 116 receives MR image 107 and PET image 115, and applies a trained neural network, such as a trained deep learning neural network as described herein, to the MR image 107 and PET image 115 to generate an attenuation map 105. For example, the neural network can be trained based on previously generated MR images and corresponding PET images (e.g., ground truth data) during a training period, and further validated during a validation period, such as by comparing attenuation maps 105 to expected attenuation maps. Further, neural network engine 116 may generate features based on the MR image 107 and PET image 115, and may provide the generated features to the trained neural network to generate the attenuation map 105.

Image volume reconstruction engine 118 obtains PET image 115 and the generated attenuation map 105, and reconstructs a final image volume 191. For example, image volume reconstruction engine 118 can apply the attenuation map 105 to PET image 115 to generate the final image volume 191. Final image volume 191 is a "corrected" PET image. In some examples, image volume reconstruction engine 118 may parse the attenuation map 105 to extract attenuation correction values, and adjusts corresponding values within PET image 115 to generate final image volume 191. Final image volume 191 can include image data that can be provided for display and analysis, for example.

Figure 7:
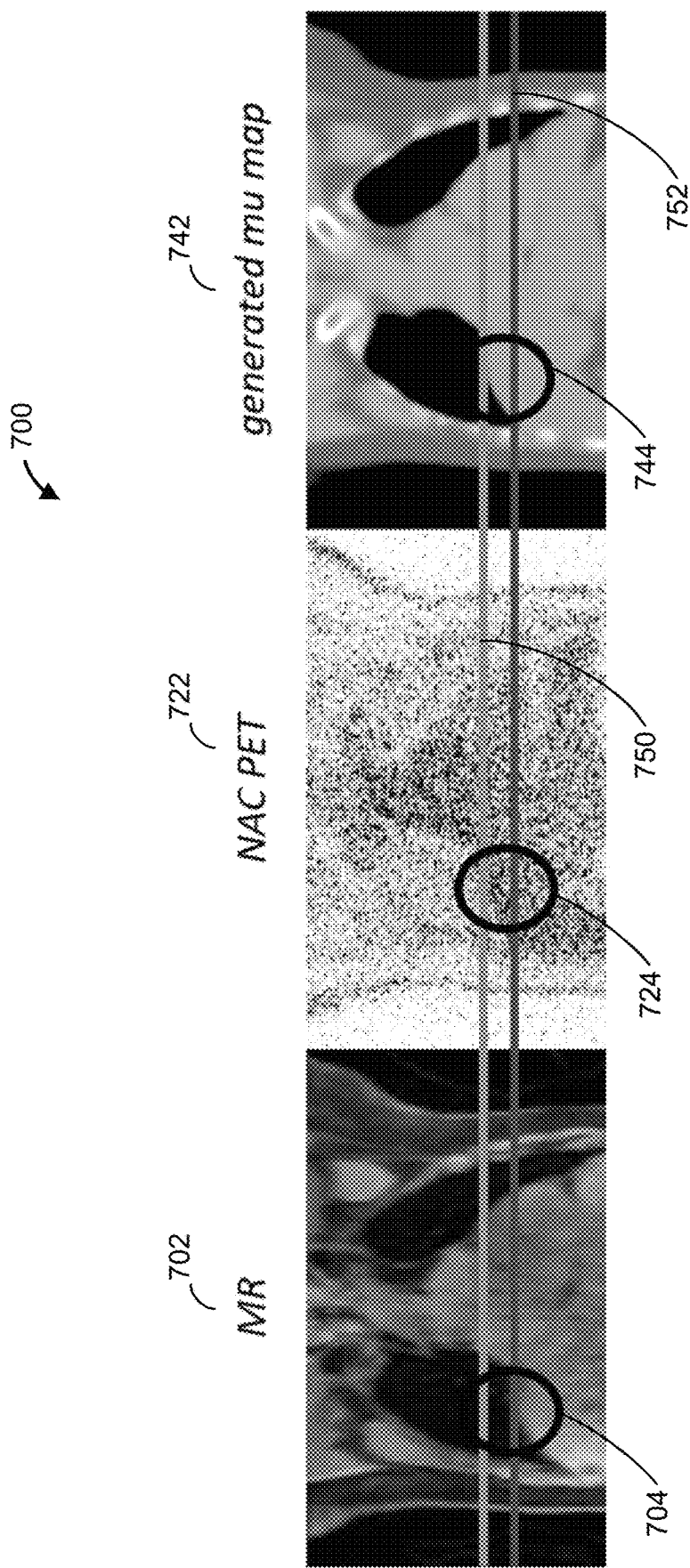
FIG. 7 is an exemplary attenuation correction map generated by the nuclear image reconstruction system of FIG. 1, in accordance with some embodiments.

FIG. 7 illustrates an image of an exemplary attenuation map 742 (e.g., mu map) that may be generated by nuclear imaging system 100 based on an MR image 702 and a PET image 722, such as an MR image and PET image captured from a PET/MR scanner. In this example, first line 750 matches a liver reference area 744 in the attenuation map 742 to a corresponding area 724 in PET image 722. Second line 752 matches the liver reference area 744 in the attenuation map 742 to a corresponding area 704 in the MR image 702. For example, within area 704 of MR image 702 between first line 750 and second line 752, no organ appears (e.g., the second line 752 appears to be just on top of tan organ, such as the liver). However, within area 724 of PET image 722, an organ (e.g., liver) appears between first line 750 and second line 752. By operating on both MR image 702 and PET image 722, the neural network engine 116 may generate attenuation map 742 that includes attenuation correction values for the corresponding area 744, thus properly indicating the organ in the area 744. Thus, nuclear imaging system 100 may generate a more accurate attenuation map regardless of which modality is used as the "anatomical prior," and can more accurately spatially match MR measurement data to the PET frame of reference.

Figure 3A:
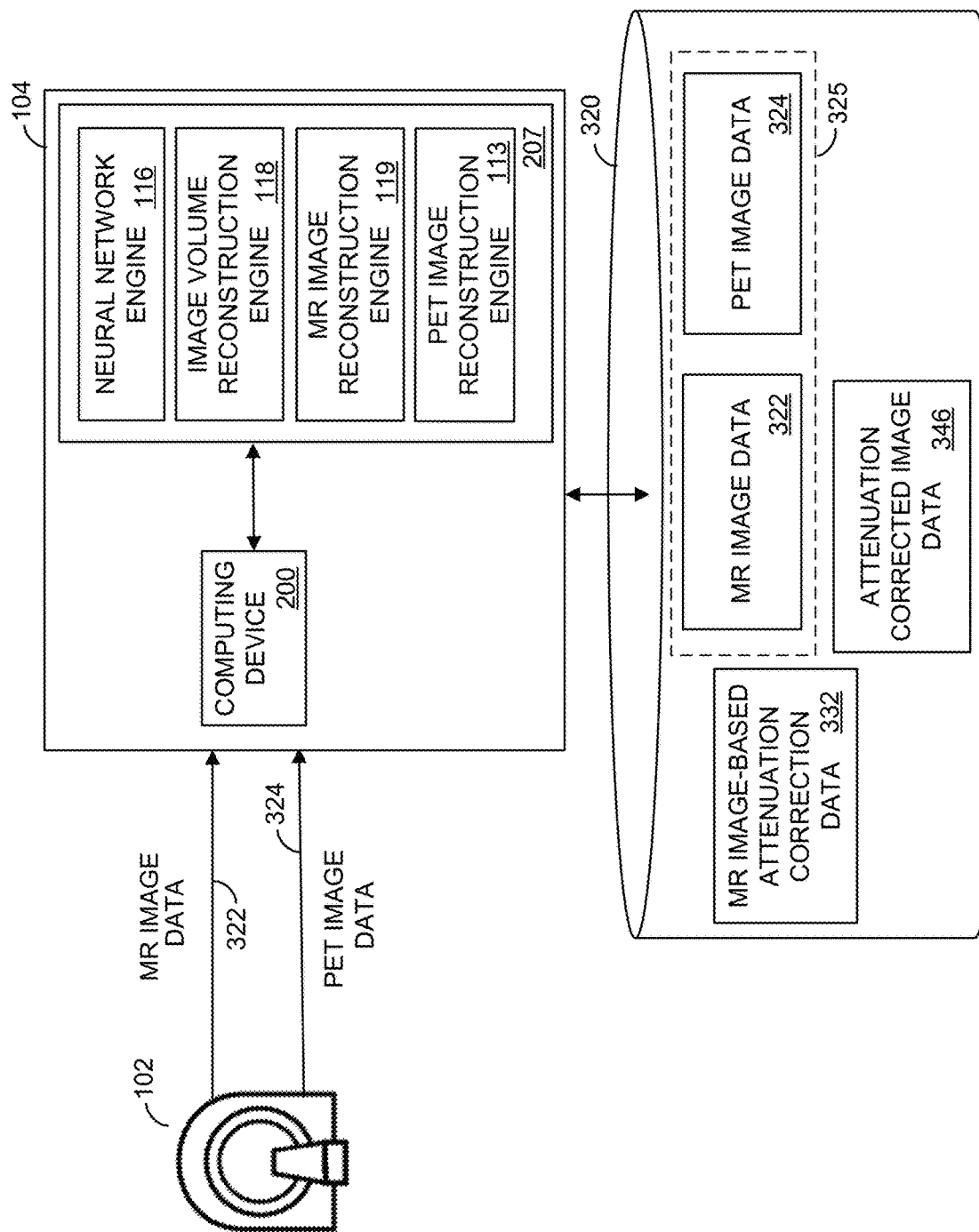
FIGS. 3A and 3B illustrate the training of neural networks in nuclear imaging systems, in accordance with some embodiments.

FIG. 3A illustrates the training of a neural network configured to generate attenuation maps 105 based on MR image data 322 and PET image data 324. MR image data 322 may characterize MR measurement data, while PET image data 324 may characterize corresponding PET measurement data. In some examples, MR measurement data and corresponding PET measurement data are generated based on scans from a same patient. In this example, computing device 200 receives MR image data 322 and PET image data 324 from image scanning system 102, and aggregates and stores MR image data 322 and PET image data 324 within data repository 320 to generate PET/MR training data 325. Computing device 200 may then obtain PET/MR training data 325, which comprises MR image data 322 and PET image data 324, and provides the PET/MR training data 325 to neural network engine 116 to train the neural network. For example, neural network engine 116 may generate features based on the PET/MR training data 325, and train the neural network based on the generated features.

In some examples, computing device 200 may perform operations to validate the neural network. For example, the computing device 200 may apply the neural network to MR images and PET images obtained from a validation test data set (e.g., stored in data repository 320) to generate a predicted attenuation correction map. The computing device 200 can further determine a loss between the predicted attenuation map and an expected attenuation map. Training of the neural network can be complete with the loss has been minimized to at least a threshold (e.g., to below a predetermined threshold).

Once trained, the neural network engine 116 can apply the trained neural network to an MR image generated from MR image data 322 and to a PET image generated from PET measurement data 324 to generate MR image-based attenuation correction data 332, which may characterize an attenuation correction map (e.g., mu map). For example, MR image reconstruction engine 119 can generate an MR image based on the MR image data 322, and PET image reconstruction engine 113 can generate a PET image based on the PET measurement data 324. In some examples, computing device 200 receives the MR image-based attenuation correction data 332 from neural network engine 116, and stores the MR image-based attenuation correction data 332 in data repository 320. Further, image volume reconstruction engine 118 may generate attenuation corrected image data 346 characterizing a final image volume based on the MR image-based attenuation correction data 332 received from neural network 116 and the PET image. Computing device 200 may store the attenuation corrected image data 346 within data repository 320.

Referring to FIG. 1B, as noted above, in this example image scanning system 102 is a PET/CT scanner that can capture PET and CT images. Image scanning system 102 can capture the CT images (e.g., of a person), and generate CT measurement data 133 based on the CT scans. Image scanning system 102 can also capture PET images (e.g., of the person), and generate PET measurement data 111 (e.g., sinogram data) based on the captured PET images. The PET measurement data 111 can represent anything imaged in the scanner's field-of-view (FOV) containing positron emitting isotopes. For example, the PET measurement data 111 can represent whole-body image scans, such as image scans from a patient's head to thigh. Image scanning system 102 can transmit the CT measurement data 133 and the PET measurement data 111 to image reconstruction system 104.

In this example, image reconstruction system 104 includes neural network engine 116, CT image reconstruction engine 139, PET image reconstruction engine 113, and image volume reconstruction engine 118. CT image reconstruction engine 139 operates on CT measurement data 133 (e.g., CT raw data) to generate reconstructed CT image 137. CT image reconstruction engine 139 can generate reconstructed CT images 137 based on corresponding CT measurement data 133 using any suitable method known in the art. PET image reconstruction engine 113 operates on PET measurement data 111 to generate reconstructed PET image 115.

Further, neural network engine 116 receives CT image 137 and PET image 115, and applies a trained neural network, such as a trained deep learning neural network as described herein, to the CT image 137 and the PET image 115 to generate an attenuation map 105. For example, the neural network can be trained based on previously generated CT images and PET images (e.g., ground truth data) during a training period, and further validated during a validation period, such as by comparing attenuation maps 105 to expected attenuation maps. In some examples, neural network engine 116 can generate features based on the CT image 137 and the PET image 115, and may provide the generated features to the trained neural network to generate the attenuation maps 105.

Image volume reconstruction engine 118 obtains PET image 115 and the generated attenuation map 105, and reconstructs a final image volume 191. For example, image volume reconstruction engine 118 applies the attenuation map 105 to the PET image 115 to generate the final image volume 191. Final image volume 191 can include image data that can be provided for display and analysis, for example.

Figure 3B:
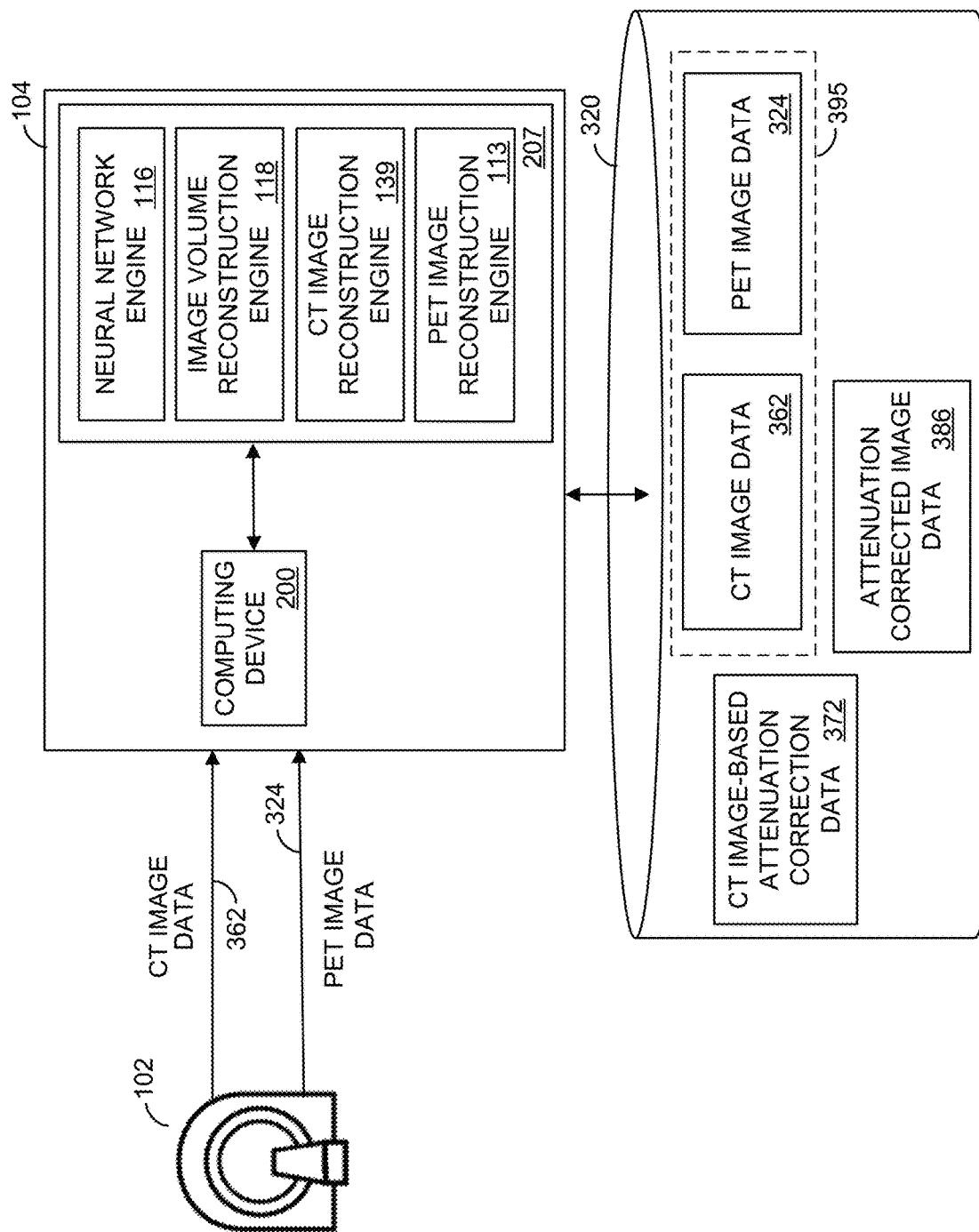

FIG. 3B illustrates the training of a neural network configured to generate attenuation maps 105 based on CT image data 362 and PET image data 324. CT image data 362 may characterize CT measurement data, while PET image data 324 may characterize corresponding PET measurement data. In some examples, CT measurement data and corresponding PET measurement data are generated based on scans from a same patient. In this example, computing device 200 receives CT image data 362 and PET image data 324 from image scanning system 102, and aggregates and stores CT image data 362 and PET image data 324 within data repository 320 to generate PET/CT training data 395. Computing device 200 may then obtain PET/CT training data 395, which comprises CT image data 362 and PET image data 324, and provides the PET/CT training data 395 to neural network engine 116 to train the neural network. For example, neural network engine 116 may generate features based on the PET/CT training data 395, and train the neural network based on the generated features.

In some examples, computing device 200 may perform operations to validate the neural network. For example, the computing device 200 may apply the neural network to CT images and PET images obtained from a validation test data set (e.g., stored in data repository 320) to generate a predicted attenuation correction map. The computing device 200 can further determine a loss between the predicted attenuation map and an expected attenuation map. Training of the neural network can be complete with the loss has been minimized to at least a threshold (e.g., to below a predetermined threshold).

Once trained, the neural network engine 116 can apply the trained neural network to a CT image generated from CT image data 362 and to a PET image generated from PET measurement data 324 to generate CT image-based attenuation correction data 372, which may characterize an attenuation correction map (e.g., mu map). For example, CT image reconstruction engine 139 can generate a CT image based on the CT image data 362, and PET image reconstruction engine 113 can generate a PET image based on the PET image data 324. In some examples, computing device 200 receives the CT image-based attenuation correction data 372 from neural network engine 116, and stores the CT image-based attenuation correction data 372 in data repository 320. Further, image volume reconstruction engine 118 may generate attenuation corrected image data 386 characterizing a final image volume based on the CT image-based attenuation correction data 372 received from neural network 116 and the PET image. Computing device 200 may store the attenuation corrected image data 386 within data repository 320.

Figure 4:
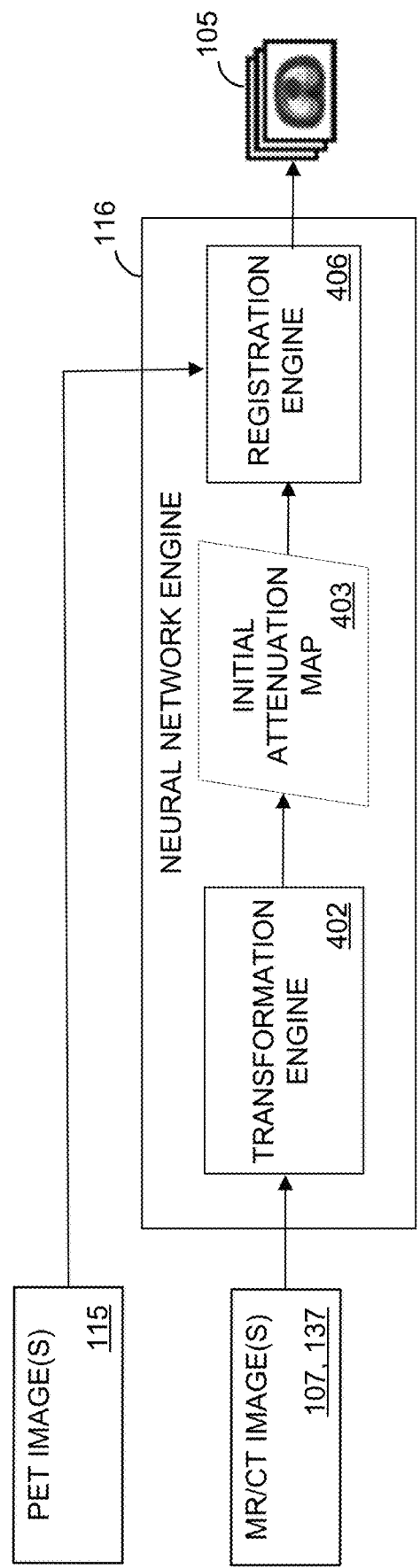
FIG. 4 illustrates further details of exemplary portions of the nuclear image reconstruction system of FIG. 1, in accordance with some embodiments.

FIG. 4 illustrates details of an exemplary neural network engine 116 that includes a transformation engine 402 and a registration engine 406. As illustrated, transformation engine 402 receives anatomy images, such as MR image 107 or CT image 137 (e.g., from MR image reconstruction engine 119 or CT reconstruction engine 139, respectively), and performs operations to generate an initial attenuation map 403. For example, transformation engine 402 may perform any known processes for generating a mu map. Further, registration engine 406 may receive initial attenuation map 403 from transformation engine 402, and PET image 115 (e.g., from PET image reconstruction engine 113), to generate an enhanced attenuation map 105.

For example, registration engine 406 may perform operations to correspond the values of the initial attenuation map 403 to the PET image 115 in a same coordinate system, and adjust the values of the initial attenuation map 403 based on corresponding values of the PET image 115. Further, registration engine 406 generates the enhanced attenuation map 105 based on the determined adjustment. For example, registration engine 406 can include a neural network which takes as input a "moving" anatomy image, e.g. initial attenuation map 403, and the "fixed" uncorrected PET image, e.g., PET image 115. Application of the neural network to the anatomy image and the uncorrected PET image causes a regression of transformation parameters necessary to match the anatomy image (e.g., moving image) to the uncorrected PET image (e.g., fixed image).

Figure 5:
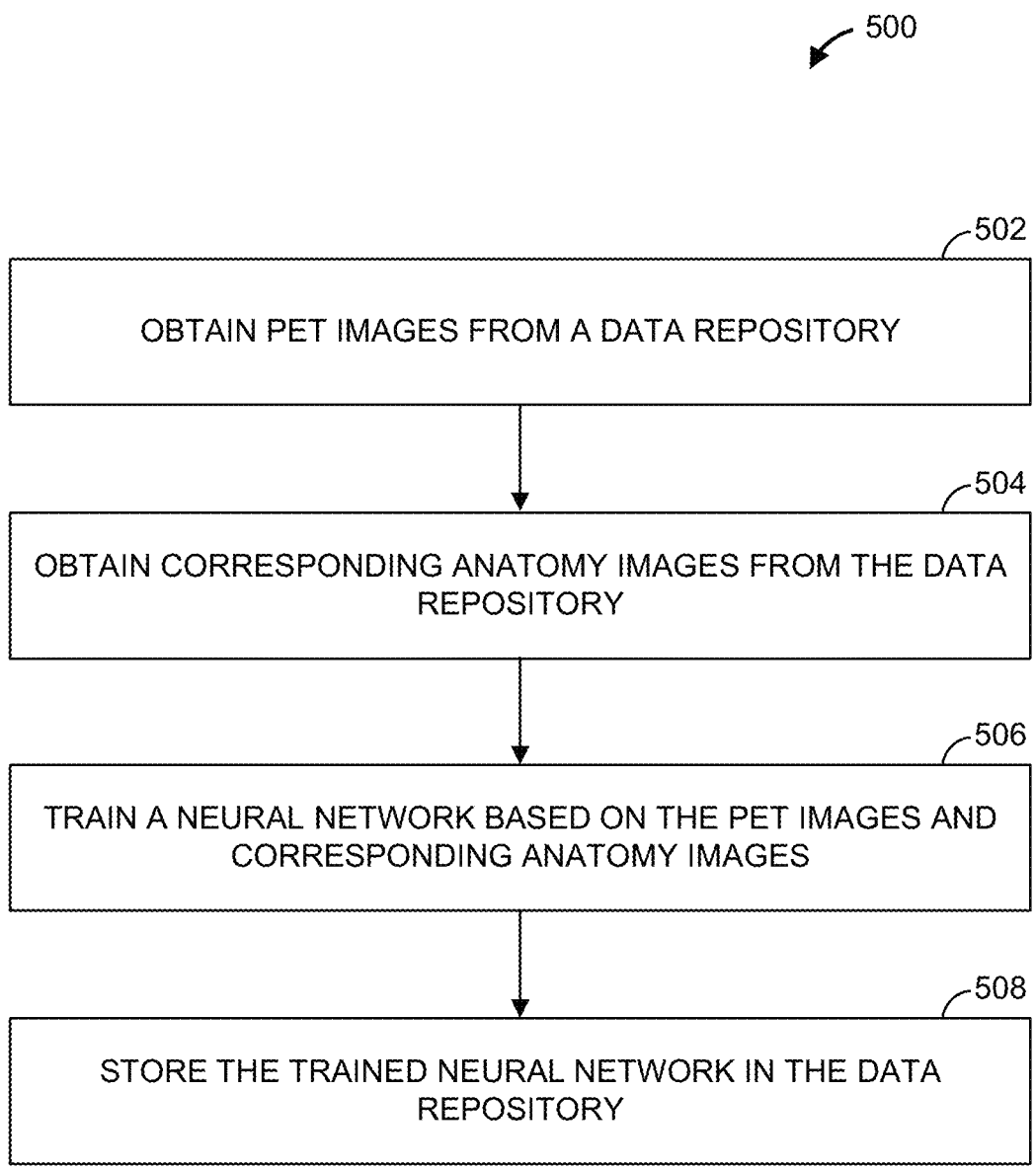
FIG. 5 is a flowchart of an example method to train a neural network, in accordance with some embodiments.

FIG. 5 is a flowchart of an example method 500 to train a neural network. The method can be performed by one or more computing devices, such as computing device 200. Beginning at step 502, PET images, such as PET images 115, are obtained from a data repository (e.g., data repository 320). At step 504, corresponding anatomy images are obtained from the data repository. The anatomy images can be, for example, MR images 107. As another example, the anatomy imaged can be CT images 137.

Further, and at step 506, a neural network is trained based on the PET images and the corresponding anatomy images. For example, image scanning system 102 may train a neural network with the PET images and MR or CT images. At step 508, the trained neural network is stored in a data repository. For example, image scanning system 102 may store the trained neural network in data repository 320, or within an internal memory of neural network engine 116, for example. The method then ends.

Figure 6:
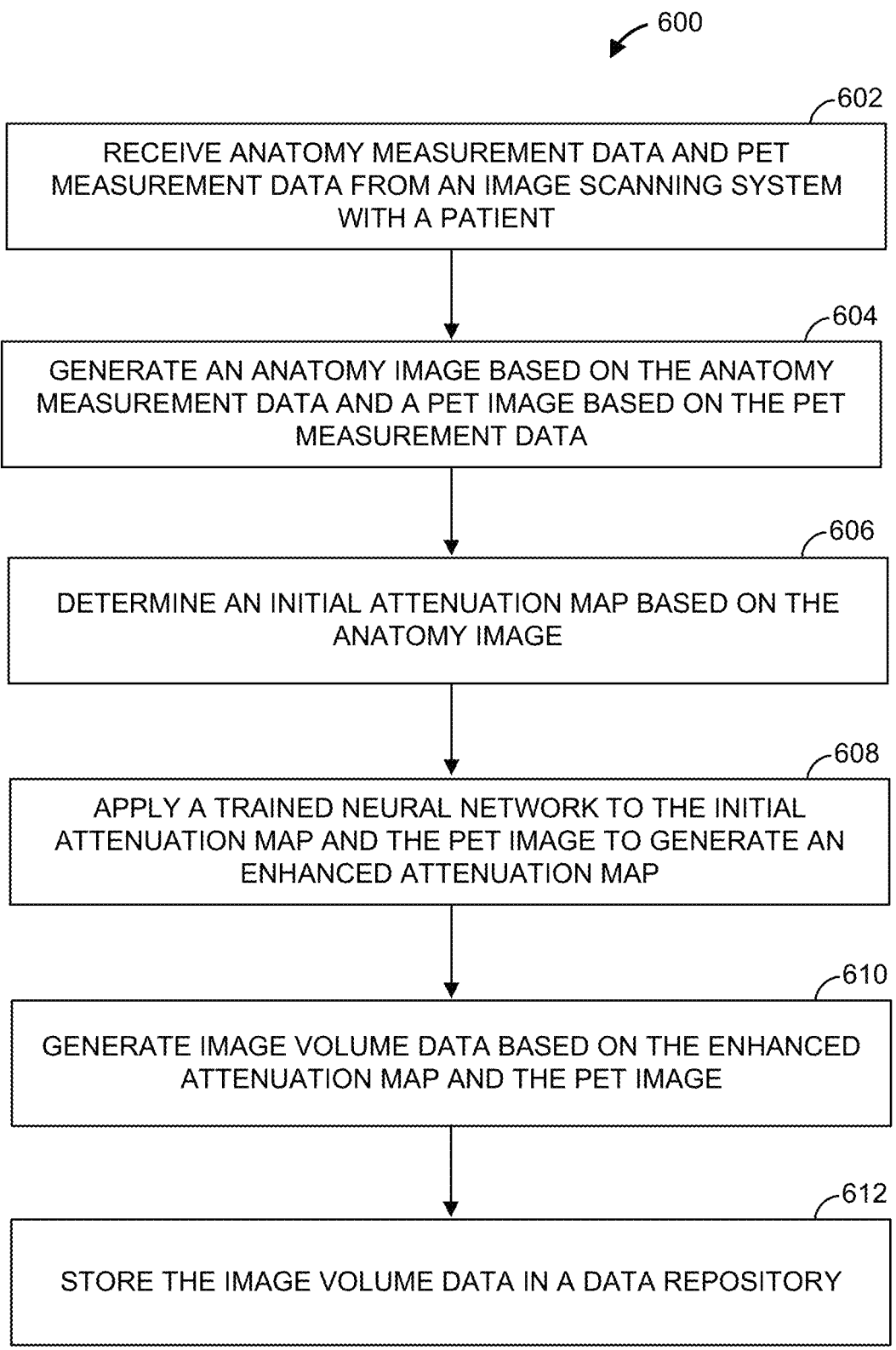
FIG. 6 is a flowchart of an example method to reconstruct an image, in accordance with some embodiments.

FIG. 6 is a flowchart of an example method 600 to generate a corrected image (e.g., an image volume), and can be carried out by one or more computing device such as, for example, computing device 200. Beginning at step 602, anatomy measurement data and PET measurement data (e.g., sinogram data) is received from an image scanning system. The anatomy measurement data can correspond to MR or CT scans of a patient, and the PET measurement data can correspond to PET scans of the patient. For example, image reconstruction system 104 can receive MR measurement data 103 and PET measurement data 111 from image scanning system 102 for a patient. At step 604, an anatomy image is generated based on the anatomy measurement data, and a PET image is generated based on the PET measurement data.

Proceeding to step 606, an initial attenuation map is determined based on the anatomy image. For example, transformation engine 402 of neural network engine 116 may generate an initial attenuation map 403 based on MR measurement data 103 (or CT measurement data 133). Further, and at step 608, a trained neural network is applied to the initial attenuation map and the PET image to generate an enhanced attenuation map. The neural network could have been trained in accordance with method 500, for example. As an example, registration engine 406 may register initial attenuation map 403 to PET image 115, and generate attenuation map 105 based on the registration.

At step 610, image volume data is generated based on the enhanced attenuation map and the PET image. The image volume data can identify and characterize an image volume (e.g., a 3D image volume). For example, image reconstruction system 104 can generate final image volume 191 based on attenuation maps 105 and corresponding PET image 115. At step 612, the final image volume is stored in a database. For example, image reconstruction system 104 can store the generated final image volume 191 in database 320. The method then ends.

In some examples, a computer-implemented method includes receiving positron emission tomography (PET) measurement data and anatomy measurement data from an image scanning system. The method further includes generating PET images based on the PET measurement data and anatomy images based on the anatomy measurement data. The method also includes training a neural network with the PET images and the anatomy images. Further, the method includes storing the trained neural network in a data repository.

In some examples, the method includes receiving additional PET measurement data and additional anatomy measurement data from the image scanning system, and generating an additional PET image based on the PET measurement data and an additional anatomy image based on the additional anatomy measurement data. The method also includes applying the trained neural network to the additional PET image and the additional anatomy image to determine an attenuation map. In some examples, the method includes generating a corrected image based on the attenuation map and the additional PET image.

In some examples, the attenuation map is an enhanced attenuation map, and the method includes determining an initial attenuation map based on the additional anatomy image, and registering the initial attenuation map to the additional PET image. The method further includes generating the enhanced attenuation map based on the registration, and generating the corrected image based on the enhanced attenuation map.

In some examples, the method includes providing the corrected image for display.

In some examples, training the neural network includes determining a loss between an output attenuation map of the neural network and an expected attenuation map, and determining the neural network is trained when the loss is beyond a threshold.

In some examples, the neural network is a deep learning neural network. In some examples, the anatomy measurement data is magnetic resonance (MR) measurement data. In some examples, the anatomy measurement data is computed tomography (CT) measurement data.

In some examples, a non-transitory computer readable medium stores instructions that, when executed by at least one processor, cause the at least one processor to perform operations including receiving positron emission tomography (PET) measurement data and anatomy measurement data from an image scanning system. The operations further include generating PET images based on the PET measurement data and anatomy images based on the anatomy measurement data. The operations also include training a neural network with the PET images and the anatomy images. Further, the operations include storing the trained neural network in a data repository.

In some examples, the operations include receiving additional PET measurement data and additional anatomy measurement data from the image scanning system, and generating an additional PET image based on the PET measurement data and an additional anatomy image based on the additional anatomy measurement data. The operations also include applying the trained neural network to the additional PET image and the additional anatomy image to determine an attenuation map. In some examples, the operations include generating a corrected image based on the attenuation map and the additional PET image.

In some examples, the attenuation map is an enhanced attenuation map, and the operations include determining an initial attenuation map based on the additional anatomy image, and registering the initial attenuation map to the additional PET image. The operations also include generating the enhanced attenuation map based on the registration, and generating the corrected image based on the enhanced attenuation map.

In some examples, the operations include providing the corrected image for display.

In some examples, training the neural network includes determining a loss between an output attenuation map of the neural network and an expected attenuation map, and determining the neural network is trained when the loss is beyond a threshold.

In some examples, the neural network is a deep learning neural network. In some examples, the anatomy measurement data is magnetic resonance (MR) measurement data. In some examples, the anatomy measurement data is computed tomography (CT) measurement data.

In some examples, a system comprises a database and at least one processor communicatively coupled to the database. The at least one processor is configured to receive positron emission tomography (PET) measurement data and anatomy measurement data from an image scanning system. The at least one processor is further configured to generate PET images based on the PET measurement data and anatomy images based on the anatomy measurement data. The at least one processor is also configured to train a neural network with the PET images and the anatomy images. Further, the at least one processor is configured to store the trained neural network in a data repository.

In some examples, the at least one processor is configured to receive additional PET measurement data and additional anatomy measurement data from the image scanning system, and generate an additional PET image based on the PET measurement data and an additional anatomy image based on the additional anatomy measurement data. The at least one process is also configured to apply the trained neural network to the additional PET image and the additional anatomy image to determine an attenuation map. In some examples, the at least one processor is configured to generate a corrected image based on the attenuation map and the additional PET image.

In some examples, the attenuation map is an enhanced attenuation map, and the at least one processor is configured to determine an initial attenuation map based on the additional anatomy image, and register the initial attenuation map to the additional PET image. The at least one processor is also configured to generate the enhanced attenuation map based on the registration, and generate the corrected image based on the enhanced attenuation map.

In some examples, the at least one processor is configured to provide the corrected image for display.

In some examples, training the neural network includes determining a loss between an output attenuation map of the neural network and an expected attenuation map, and determining the neural network is trained when the loss is beyond a threshold.

In some examples, the neural network is a deep learning neural network. In some examples, the anatomy measurement data is magnetic resonance (MR) measurement data. In some examples, the anatomy measurement data is computed tomography (CT) measurement data.

The apparatuses and processes are not limited to the specific embodiments described herein. In addition, components of each apparatus and each process can be practiced independent and separate from other components and processes described herein.

The previous description of embodiments is provided to enable any person skilled in the art to practice the disclosure. The various modifications to these embodiments will be readily apparent to those skilled in the art, and the generic principles defined herein can be applied to other embodiments without the use of inventive faculty. The present disclosure is not intended to be limited to the embodiments shown herein, but is to be accorded the widest scope consistent with the principles and novel features disclosed herein.

What is claimed is:

1. A computer-implemented method comprising:
   receiving positron emission tomography (PET) measurement data and anatomy measurement data from an image scanning system;
   generating PET images based on the PET measurement data and anatomy images based on the anatomy measurement data;
   training a neural network with the PET images and the anatomy images, the neural network comprising a transformation stage and a registration stage, wherein the training configures the transformation stage to generate initial attenuation maps based on the anatomy measurement data, and the training configures the registration stage to generate final attenuation maps based on the initial attenuation maps and the PET images;
   generating attenuation maps based on the training; and
   storing the trained neural network in a data repository.

2. The computer-implemented method of claim 1 further comprising:
   receiving additional PET measurement data and additional anatomy measurement data from the image scanning system;
   generating an additional PET image based on the additional PET measurement data and an additional anatomy image based on the additional anatomy measurement data; and
   applying the trained neural network to the additional PET image and the additional anatomy image to determine an attenuation map.

3. The computer-implemented method of claim 2 further comprising generating a corrected image based on the attenuation map and the additional PET image.

4. The computer-implemented method of claim 3 wherein the attenuation map is an enhanced attenuation map, the method further comprising:
   determining an initial attenuation map based on the additional anatomy image;
   registering the initial attenuation map to the additional PET image;
   generating the enhanced attenuation map based on the registration; and generating the corrected image based on the enhanced attenuation map.

5. The computer-implemented method of claim 3 further comprising providing the corrected image for display.

6. The computer-implemented method of claim 1, wherein training the neural network comprises:
determining a loss between an output attenuation map of the neural network and an expected attenuation map; and
determining the neural network is trained when the loss is less a threshold.

7. The computer-implemented method of claim 1 wherein the neural network is a deep learning neural network.

8. The computer-implemented method of claim 1 wherein the anatomy measurement data is magnetic resonance (MR) measurement data.

9. The computer-implemented method of claim 1 wherein the anatomy measurement data is computed tomography (CT) measurement data.

10. A non-transitory computer readable medium storing instructions that, when executed by at least one processor, cause the at least one processor to perform operations comprising:
receiving positron emission tomography (PET) measurement data and anatomy measurement data from an image scanning system;
generating PET images based on the PET measurement data and anatomy images based on the anatomy measurement data;
training a neural network with the PET images and the anatomy images, the neural network comprising a transformation stage and a registration stage, wherein the training configures the transformation stage to generate initial attenuation maps based on the anatomy measurement data, and the training configures the registration stage to generate final attenuation maps based on the initial attenuation maps and the PET images;
generating attenuation maps bases on the training; and
storing the trained neural network in a data repository.

11. The non-transitory computer readable medium of claim 10 storing instructions that, when executed by at least one processor, further cause the at least one processor to perform operations comprising:
receiving additional PET measurement data and additional anatomy measurement data from the image scanning system;
generating an additional PET image based on the additional PET measurement data and an additional anatomy image based on the additional anatomy measurement data; and
applying the trained neural network to the additional PET image and the additional anatomy image to determine an attenuation map.

12. The non-transitory computer readable medium of claim 11 storing instructions that, when executed by at least one processor, further cause the at least one processor to perform operations comprising generating a corrected image based on the attenuation map and the additional PET image.

13. The non-transitory computer readable medium of claim 12 wherein the attenuation map is an enhanced attenuation map, and further storing instructions that, when executed by at least one processor, further cause the at least one processor to perform operations comprising:
determining an initial attenuation map based on the additional anatomy image;
registering the initial attenuation map to the additional PET image;
generating the enhanced attenuation map based on the registration; and
generating the corrected image based on the enhanced attenuation map.

14. The non-transitory computer readable medium of claim 10 storing instructions that, when executed by at least one processor, further cause the at least one processor to perform operations comprising:
determining a loss between an output attenuation map of the neural network and an expected attenuation map; and
determining the neural network is trained when the loss is less a threshold.

15. The non-transitory computer readable medium of claim 10 wherein:
the neural network is a deep learning neural network; and
the anatomy measurement data is one of magnetic resonance (MR) measurement data and computed tomography (CT) measurement data.

16. A system comprising:
a database; and
at least one processor communicatively coupled to the database and configured to:
receive positron emission tomography (PET) measurement data and anatomy measurement data from an image scanning system;
generate PET images based on the PET measurement data and anatomy images based on the anatomy measurement data;
train a neural network with the PET images and the anatomy images, the neural network comprising a transformation stage and a registration stage, wherein the transformation stage is configured to generate initial attenuation maps based on the anatomy measurement data, and the registration stage is configured to generate final attenuation maps based on the initial attenuation maps and PET images,
generate attenuation maps based n the training; and
store the trained neural network in a data repository.

17. The system of claim 16, wherein the at least one processor is configured to:
receive additional PET measurement data and additional anatomy measurement data from the image scanning system;
generate an additional PET image based on the PET measurement data and an additional anatomy image based on the additional anatomy measurement data; and
apply the trained neural network to the additional PET image and the additional anatomy image to determine an attenuation map.

18. The system of claim 17, wherein the at least one processor is configured to generate a corrected image based on the attenuation map and the PET measurement data.

19. The system of claim 18, wherein the at least one processor is configured to:
determine an initial attenuation map based on the additional anatomy image;
register the initial attenuation map to the additional PET image;
generate the enhanced attenuation map based on the registration; and
generate the corrected image based on the enhanced attenuation map.

20. The system of claim 16, wherein training the neural network comprises:
- determining a loss between an output attenuation map of the neural network and an expected attenuation map; and
- determining the neural network is trained when the loss is a threshold.

* * * * *